US00PP18666P2

(12) United States Plant Patent
Bradford

(10) Patent No.: US PP18,666 P2
(45) Date of Patent: Mar. 25, 2008

(54) INTERSPECIFIC TREE NAMED 'PLUMSWEET IX'

(50) Latin Name: ***Prunus* sp.**
Varietal Denomination: PLUMSWEET IX

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,858

(22) Filed: Dec. 7, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

| | | | |
|---|---|---|---|
| PP8,498 | P | 12/1993 | Bradford et al. |
| PP14,219 | P2 | 10/2003 | Bradford |
| PP15,235 | P2 | 10/2004 | Bradford |

*Primary Examiner*—Kent Bell
*Assistant Examiner*—S B McCormick-Ewoldt

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, interspecific, or plum that blooms during the mid to late season. The fruit matures under the ecological conditions described during late August, with first picking on Aug. 24, 2006. The fruit is uniformly large in size, a yellowish green and red two-tone in skin color, semi-freestone in type, globose to somewhat cordate is shape, mostly red in flesh color, firm in texture, and excellent in flavor.

1 Drawing Sheet

Botanical classification: *Prunus* sp.
Varietal denomination: 'PLUMSWEET IX'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'PLUMSWEET IX'.

During a typical blooming season I isolate as seed parents both individual and groups of different plum tress by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 1999 one such house containing 'BRADGREEN' (U.S. Plant Pat. No. 8,498) plum was crossed by me in this manner. To pollinate this plum, I selected bouquets from several sources of apricot and interspecific plum-apricot hybrid trees without keeping specific written details. Upon reaching maturity the fruit from this plum tree was harvested, and the seeds were removed, cracked, stratified and germinated as a group with the label "H9". They were grown as seedlings on their own root in my greenhouse and upon reaching dormancy transplanted to a cultivated area of my experimental orchard located near Le Grand, Calif. in Merced County (San Joaquin Valley). During the summer of 2002 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'BRADGREEN' (U.S. Plant Pat. No. 8,498) plum by being self-unfruitful and by producing fruit that is large in size and sweet in flavor, but is quite distinguished therefrom by blooming much later and by producing fruit that is a two-tone red and yellowish green in skin color, that has significant red in the flesh color, and that matures about two weeks earlier.

The present variety is most similar to 'PLUMSWEET-THREE' (U.S. Plant Pat. No. 15,235) interspecific plum tree by being self-unfruitful and by producing fruit that is a red and yellowish green two-tone in skin color, semi-freestone in type, and large in size, but is distinguished therefrom by producing fruit that has a significant amount of red in the flesh color and that matures about six days later.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the mid to late season, such as 'Plumsweetone' (U.S. Plant Pat. No. 14,219) plum. The present variety's abundance of blossoms and pollen entices strong bee activity to facilitate pollination. The fruit matures under the ecological conditions described during late August, with first picking on Aug. 24, 2006. The fruit is uniformly large in size, a yellowish green and red two-tone in skin color, semi-freestone in type, globose to somewhat cordate in shape, significantly red in flesh color, firm in texture, and excellent in flavor.

DRAWING

The accompanying photograph consists of four whole fruits positioned to display the characteristics of the skin color and form, one fruit divided transversely to the suture plane to reveal the flesh and stone, typical leaves, and insets displaying the buds and blossoms on the tree.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Aug. 28, 2006, on the original tree during its seventh growing season. The flower and bud descriptions were developed during the previous blooming season. All major color code designations are by reference to the Inter-Society Color Council, National Bureau of Standards. Common color names are also used occasionally.

Parentage:
- *Seed parent.* —'Bradgreen' (USPP8498).
- *Pollen parent.* —Unknown.

Tree

Size: Medium, reaching and maintaining a height of 8' [2.44 m.] and a spread of 6' [1.83 m.] after seven growing seasons utilizing typical dormant pruning.

Vigor: Medium, responding typically to irrigation and fertilization. The variety grows about 3' [0.91 m.] of surplus top-growth during the spring and summer. The plant should be grown on a standard commercial rootstock for production purposes.

Growth: Spreading and open.

Form: Pruned to a perpendicular "V".

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'Plumsweetone' (U.S. Plant Pat. No. 14,219).

Bearing: Regular bearer when weather during the blooming season is warm and dry enough for sufficient bee activity for pollination.

Trunk:
- *Size.*—Medium, reaching a maximum diameter of 3¾" [95 mm.] after the seventh growing season.
- *Texture.*—Shaggy.
- *Bark color.*—A Brownish gray [64. brGy] and Moderate brown [58. m.Br] variegation with Light yellowish brown [76. l.yBr] crevices present.
- *Lenticels.*—Approximate Number Per Square Inch: 8. Color: Strong orange yellow [68. s.OY]. Typical Size: 3/16" [4.8 mm.] to 7/16" [11.1 mm.]. Shape: Eye-shaped to elongated.

Branches:
- *Size.*—Diameter of limb is 2½" [64 mm.] measured 12" above the crotch, 1⅜" [35 mm.] measured 12" above the first fork.
- *Texture.*—Smooth on first and second year wood, increasing roughness with age.
- *Color.*—1st Year Wood Topside: Strong brown [55. s.Br]. 1st Year Wood Underside: Light yellow green [119. l.YG]. Older Wood: Deep yellowish brown [75. deep yBr].
- *Lenticels.*—Number Per Square Inch: More than 50 on second year wood. Color: Moderate orange yellow [71. m.OY]. Typical size: 1/32" [0.8 mm.] to 3/32" [2.4 mm.]. Shape: Elongated.

Leaves:
- *Size.*—Medium. Average Length: 4⅜" [111 mm.]. Average width: 1⅞ [48 mm.].
- *Arrangement.*—Alternate.
- *Thickness.*—Medium.
- *Form.*—Elliptical.
- *Apex.*—Acuminate.
- *Base.*—Acute with an average angle base angle of 70 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined. Color: Pale yellow green [121, p.YG].
- *Petiole.*—Average Length: ¾" [19.1 mm.]. Average Thickness: 3/32" [2.4 mm.]. Color: Dark reddish orange [38. d.rO] on the topside and Light yellow green [119. l.YG] on the underside.
- *Stipules.*—Number: 2 per leaf, up to 6 per growing tip. Average Length: ⅜" [9.5 mm.]. Color: Light yellow green [119. l.YG] becoming Brownish orange [54. brO] with age.
- *Glands.*—Number: Usually 1 or 2 per leaf. Position: Usually alternate, located at the intersection of the petiole and the leaf blade. Size: Small. Form: Globose. Color: Light yellow green [119. l.YG] becoming Grayish brown [61. gy.Br] with age.

Leaf buds: Pointed, medium.

Flower buds:
- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Color.*—White [263. White].

Flowers: Perfect, complete, perigynous, usually a single pistil, typically thirty or more stamens, five sepals and petal locations alternately positioned.
- *Average flower diameter.*—1" [25.4 mm.].
- *Number of petals.*—Five, no double blossoms observed.
- *Petal shape.*—Circular to oval.
- *Petal margin.*—Smooth.
- *Average petal diameter.*—7/16" [11.1 mm.].
- *Average petal length.*—½" [12.7 mm.].
- *Petal apex.*—Rounded.
- *Petal base.*—Rounded to somewhat obtuse.
- *Petal color.*—White [263. White].
- *Anther color.*—Brilliant yellow [83. brill.Y].
- *Stigma color.*—Pale greenish yellow [104. p.gY].
- *Sepal color.*—Brilliant yellow green [116. brill.YG] with a slight amount of Grayish purplish pink [253. gy.pPk] on the margins.
- *Sepal length.*—5/32" [4.0 mm.].
- *Sepal width.*—⅛" [3.2 mm.].

*Average pistil length.*—9/16" [14.3 mm.].
*Average stamen length.*—7/16" [11.1 mm.].
*Fragrance.*—Moderate.
*Pollen production.*—Abundant.
*Blooming period.*—Medium to late, two days after 'Santa Rosa' (unpatented).
*Onset of bloom.*—One percent on Mar. 1, 2006.
*Date of full bloom.*—Mar. 12, 2006.
*Duration of bloom.*—One to two weeks, dependent on ambient temperature.
*Bloom density.*—Very heavy.
*Number per cluster.*—2 to 10, average 5.

FRUIT

Maturity when described: Shipping ripe, Aug. 28, 2006.
Date of first picking: Aug. 24, 2006.
Date of last picking: Sep. 4, 2006.
Size: Uniform, large.
*Average diameter axially.*—2 9/16" [65 mm.].
*Average diameter across cheek plane.*—2 7/8" [73 mm.].
*Average diameter across suture plane.*—2 13/16" [71 mm.].
*Typical weight.*—6.8 ounces [193 grams.].
Form: Uniform, symmetrical, globose to cordate.
*Longitudinal section form.*—Elliptical to oval.
*Axial view.*—Round.
Suture: An inconspicuous line located in shallow groove extending from the base to apex, sharper within the stem cavity.
Ventral surface: Rounded, no lips.
Cavity: Flaring, circular to slightly elongated in the suture plane, suture showing on one side, Pale yellow [89. p.Y] stem markings on some.
*Depth.*—5/8" [15.9 mm.].
*Breadth.*—1 1/4 [31.8 mm.].
Base: Truncate, cordate if viewed parallel to the suture.
Apex: Rounded with a slight hump at the pistil point.
Pistil point: An inconspicuous dot.
Stem: Medium.
*Average length.*—5/16" [7.9 mm.].
*Average width.*—1/8" [3.2 mm.].
Skin:
*Thickness.*—Medium.
*Surface.*—Smooth.
*Tenacity.*—Tenacious to flesh.
*Taste.*—Slightly astringent.
*Tendency to crack.*—Slight.
*Color.*—Deep reddish orange [36. deep rO] mottled over a Light greenish yellow [101. l.gY] with moderate Light orange yellow [70. l.OY] freckling toward the apex.
*Boom.*—Abundant.
Flesh:
*Color.*—Light yellow [86. l.Y] with a significant amount of Moderate red [15. m.R] bleeding toward the skin.
*Surface of pit cavity.*—Grayish yellow [90. gy.Y] fibers when twisted away from stone.
*Amygdalin.*—Moderate.
*Juice.*—Abundant, rich.
*Texture.*—Firm, crisp.
*Fibers.*—Abundant, fine.
*Ripens.*—Somewhat earlier at the apex.
*Flavor.*—Mildly acidic and sweet, typically 18–20 brix.
*Aroma.*—Very slight.
*Eating quality.*—Excellent.

STONE

Type: Semi-freestone.
Form: Oval.
Hilum: Narrow.
Base: Oblique.
Apex: Acute with a sword-like tip 1/8" [3.2 mm.] in length.
Sides: Equal.
Surface: Rough throughout without grooves.
External color of stone: Light yellowish brown [76. l.yBr].
Pit wall color when cracked: Dark orange yellow [72. d.OY].
Cavity surface color: Moderate brown [58. m.Br].
Average pit wall thickness: 1/16" [1.6 mm.].
Average width: 3/4" [19.1 mm.].
Average length: 1" [25.4 mm.].
Average breadth: 7/16"[11.1 mm.].
Tendency to split: Slight.
Kernel:
*Form.*—Oval.
*Skin color.*—Pale yellow [89. p.Y] when first cracked.
*Pellicle color.*—Light grayish yellowish brown [79. l.gy.yBr].
*Vein color.*—Moderate yellowish brown [77. m.yBr].
*Taste.*—Somewhat bitter.
*Viable.*—Yes.
*Average width.*—15/32" [11.9 mm.].
*Average length.*—5/8" [15.9 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.
Resistance to heat: No damage observed following extended period of temperatures in excess of 110 degrees Fahrenheit during July of 2006.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'PLUMSWEETTHREE' (U.S. Plant Pat. No. 15,235) interspecific plum tree by being self-unfruitful and by producing fruit that is a red and yellowish green two-tone in skin color, semi-freestone in type, and large in size, but is distinguished therefrom by producing fruit that has a significant amount of red in the flesh color and that matures about six days later.

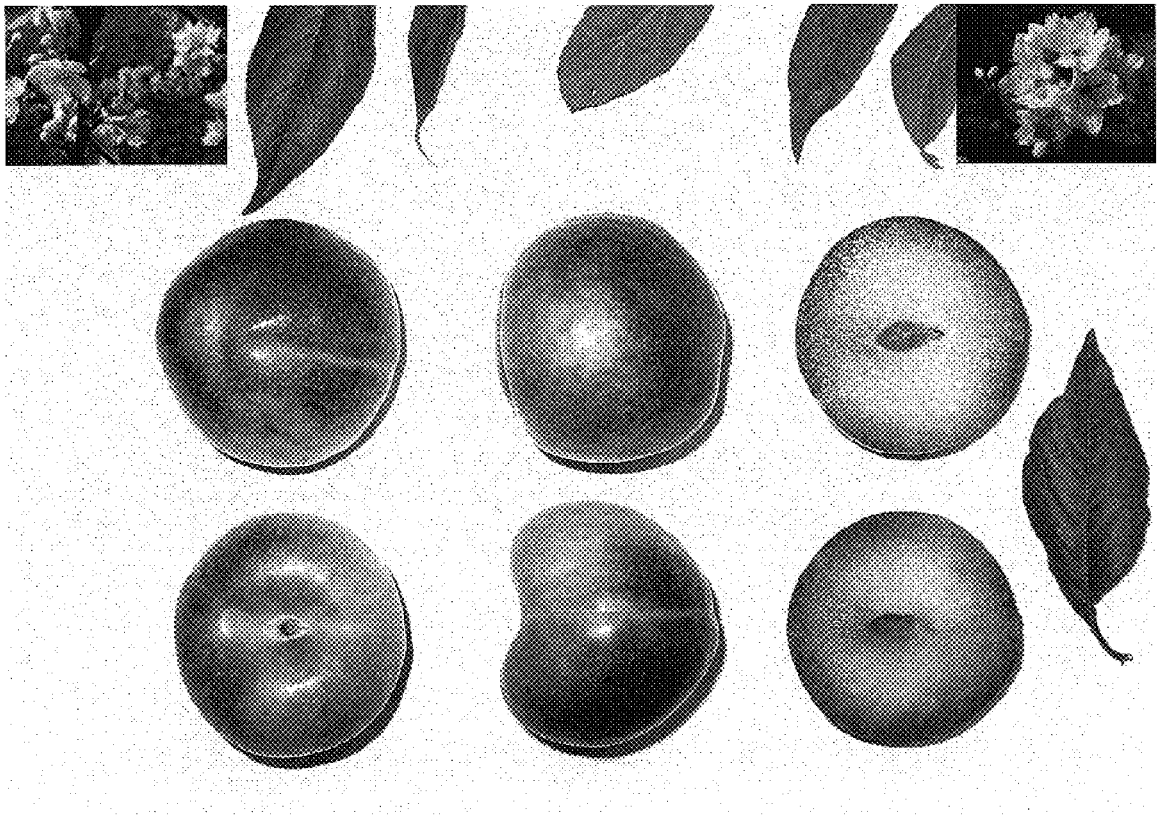

* * * * *